United States Patent [19]

Schutt

[11] 4,035,234

[45] July 12, 1977

[54] PROCESS FOR THE PREPARATION OF THE KALLIKREIN-TRYPSIN INHIBITOR

[75] Inventor: Hermann Schutt, Wuppertal, Germany

[73] Assignee: Bayer Aktiengesellschaft, Germany

[21] Appl. No.: 661,160

[22] Filed: Feb. 25, 1976

[30] Foreign Application Priority Data

Mar. 5, 1975  Germany .......................... 2509482

[51] Int. Cl.² .......................................... C07G 7/026
[52] U.S. Cl. .................................... 195/5; 195/65; 195/66 R
[58] Field of Search ................... 195/66 R, 65, 4, 5

[56] References Cited

U.S. PATENT DOCUMENTS 3,630,841  12/1971  Werle et al. ................. 195/66 R X

FOREIGN PATENT DOCUMENTS 2,447,050  10/1975  Germany .............................. 195/29

*Primary Examiner*—Lionel M. Shapiro

[57] ABSTRACT

The kallikrein-trypsin inhibitor is obtained from animal organs by proteolytic digestion of the organ at an elevated temperature and recovery of kallikrein-trypsin inhibitor by selective adsorption thereof on carrier-bound trypsin and subsequent desorption.

12 Claims, No Drawings

PROCESS FOR THE PREPARATION OF THE KALLIKREIN-TRYPSIN INHIBITOR

The present invention relates to a process for the preparation of the known biologically active kallikrein-trypsin inhibitor.

It has already been disclosed that kallikrein-trypsin inhibitor can be obtained, according to German Patent Specification No. 1,084,433, from comminuted animal organs using water-miscible organic solvents, mainly methanol, in the presence of salts or hydroxides of the alkaline earth metals. This type of selective extraction gives a relatively pure inhibitor since high-molecular weight proteins are denatured. A disadvantage of this method is, however, that the organic solvents must be recovered in explosion-proof installations. Furthermore, it is known that the yield is dependent on the degree of comminution of the organs. The yield of kallikrein-trypsin inhibitor can be increased by a repeated extraction of the organ according to the same principle.

On the other hand, it has been disclosed that the kallikrein-trypsin inhibitor can be extracted from various organs using strong acids, such as sulphuric acid (French Patent Specification No. 1,566,777), trichloroacetic acid (German Patent Specification No. 1,011,576), oxalic acid (German Patent Specification No. 1,492,114) or perchoric acid (Zeitschrift fur Physiologische Chemie (1964) 338, 228–330). The crude extracts obtained with acids are comparable in yield to that obtained with organic solvents, but not in purity (KIU/mg) (kallikrein inhibitor units); see E. K. Frey, H. Kraut and E. Werle, das Kallikrein-Kinin-System und seine Inhibitoren (The Kallikrein-Kinin System and its Inhibitors), page 11, Ferdinand Enke, Stuttgart (1968). 9. Moreover, the acid anions must be removed from the crude extract in the course of purification, e.g. by adsorption on ion exchanger material.

Further purification of the kallikrein-trypsin inhibitor from these crude solutions is effected by precipitating the inhibitor as a sparingly soluble derivative of metaphosphoric acid or polyphosphoric acid according to German Patent Specifications Nos. 1,193,200, 1,192,368 and 1,181,370. The complexes are dissociated into the components according to known methods and the solution is then freed from salts.

A procedure based on the same principle is employed in German Patent Specification No. 1,251,911, where, by adding elastin at pH 7–10, a sparingly soluble inhibitor-elastin complex is separated off, which is dissociated into its components at pH 1–6.

The seperation of the kallikrein-trypsin inhibitor from impurities with the aid of sparingly soluble derivatives is associated with slight difficulties, for example, it can be carried out only with highly concentrated and salt-free solutions. Moreover, the precipitation products are soluble in excess precipitant. Separation of the inhibitor via the elastin complex is not favorable economically.

It is therefore an object of the present invention to provide a reliable and economical process for preparing the kallikrein-trypsin inhibitor.

According to the present invention, there is provided a process for obtaining kallikrein-trypsin inhibitor comprising subjecting an animal organ containing the inhibitor to proteolysis by a proteolytic enzyme at an elevated temperature, adsorbing the resulting extract on carrier-bound trypsin and dissociating the resulting trypsin-inhibitor complex into trypsin and kallikrein-trypsin inhibitor.

The stability of the kallikrein-trypsin inhibitor towards proteolytic enzymes has indeed been described in the literature (B. Kassell, Methods in Enzymology, 19 (1970) 848 and 850), but the inhibitor was treated with proteases under comparatively mild conditions. By contrast, in the process according to the present invention, the crude extract from the animal organ is hydrolyzed in aqueous solution at an elevated temperature, and while the kallikrein-trypsin inhibitor is unaffected, the other proteins are converted to peptides and amino acids. It is extremely surprising that the kallikrein-trypsin inhibitor withstands such extreme conditions for protein hydrolysis without modification of its structure. The process according to the invention for preparation of the kallikrein-trypsin inhibitor from animal organs thus represents a significant advance in the art.

In general, when carrying out the process according to the invention, comminuted material from an animal organ, particularly organs of ruminants, preferably the lung, parotid, liver or pancreas, most preferably cattle lung, is first reacted with a proteolytic enzyme. With the exception of thermolysin and a protease obtained from hyphomycetes, it is possible to use numerous proteolytic enzymes, such as proteinase K from Tritirachium album limber, collagenase from Clostridium histolyticum or bromelain. Thermolysin and the protease obtained from hyphomycetes completely destroy the inhibitory activity of the organ extract by cleavage of the inhibitor structure. The proteolytic enzymes which can be employed for the process according to the invention are isolated from micro-organisms, fungi or plants. In contrast to trypsin, chymotrypsin, plasmin and kallikrein, the proteases are not inhibited by the kallikrein-trypsin inhibitor.

From the point of view of economics, proteolytic enzymes of the subtilisin (EC 3.4.3.16) and papain (EC 3.4.4.10) type as well as proteases from fungi of the genus Aspergillus are particularly suitable. These enzymes can be employed as commercially available industrial enzymes without prior purification. The properties of proteolytic enzymes and description of their biochemical actions are set forth in G. E. Perlman and L. Lorand, Methods in Enzymology, 19 (1970), 199–215 for subtilisin, 226–244 for papain and 581–591 for proteases from Aspergillus.

The enzymes are brought into contact with the animal organ protein at the pH which is optimum for the particular enzyme. The pH value can usually be varied within a wide range, e.g. from about pH 5 to about pH 10, without the yield and purity of the inhibitor changing significantly. Denatured proteins are better substrates for proteases than the native proteins.

While at 25° C it is possible to obtain only turbid crude extract solutions from a digestion of the lung with proteases, which solutions cannot be perfectly clarified even after the addition of filter aids, the crude solutions obtained at 60° C are clear. Further, the activity of the proteases increases about five-fold on raising the reaction temperature from 25° to 60° C, and hence the reaction temperature is preferably about 60° C. However, useful results are obtained at a temperature of at least about 40° C, and a temperature range of about 40° to about 70° C may be used to good effect. A reaction time of about 90 to about 120 minutes will also give good results.

If, in addition to the kallikrein-trypsin inhibitor, it is also intended to obtain a hydrolyzed protein in the form of a peptone from the animal organ, it is also possible to allow two proteolytic enzymes to act sequentially on the organ; preferably, subtilisin is allowed to act first and then protease P.

Subtilisin, papain and proteinase N can be quantitatively destroyed by adding concentrated sulphuric acid until the pH value reaches 1–2. In the case of protease P, a residual activity of 45% of the initial value is still found.

The extraction step, by means of which a high yield of relatively pure inhibitor is obtained, is combined with selective adsorption of the inhibitor on carrier-bound trypsin. This is carried out according to the principle of affinity chromatography, as described in German Published Specification No. 1,517,753. Constituents of the animal organ that have no affinity for trypsin, i.e. the hydrolyzed protein obtained by means of the proteolysis, are not retained by the trypsin column, whereas the kallikrein inhibitor is retained. The trypsin-inhibitor complex formed in the column is then dissociated with a dilute mineral acid at a low pH, e.g. about pH 1 to about pH 3, into its constituents trypsin and kallikrein inhibitor.

The extraction step may be carried out using ambient temperatures or with cooling. Preferably, the extract from the proteolysis of the organ is fed to the column containing carrier-bound trypsin, the hydrolyzed protein is eluted from the column with an acetate buffer of about pH 4, and then the trypsin-inhibitor complex is dissociated with dilute mineral acid at a low pH, e.g. up to about pH 3.

The trypsin can be bonded to any carrier material with which trypsin enters into a covalent bond. Examples of suitable carrier materials include Sepharose, copolymers of acrylamide, e.g. N,N'-methylene-bis-acrylamide and maleic acid, carboxymethylcellulose, cross-linked maleic anhydride, and the like.

The electrophoretic and immunological properties and the amino acid composition of the kallikrein-trypsin inhibitor obtained according to the present invention are completely identical with those of an inhibitor obtained from the same animal organ by other extraction processes or other purification methods.

The kallikrein-trypsin inhibitor is a basic protein having a molecular weight of 6513, the amino acid sequence of which is known. (Anderer F. A. and Hörnle, S, Z. Naturforsch; 20 b, 457 (1965); Anderer F. A., Z. Naturforsch; 20 b, 462 (1965); Anderer, F. A. and Hörnle, S., J. Biol. Chem. 241 1568 (1965)). The kallikrein inhibitor inhibits the enzymes trypsin (EC 3.4.4.4), chymotrypsin (EC 3.4.4.5), plasmin (EC 3.4.4.14) and kallikrein (EC 3.4.4.21). It is found in a particularly high concentration in the organs of ruminants.

The kallikrein-trypsin inhibitor obtained according to the invention can be used medically in the same way as is known from the literature, for example for the therapy of pancreatitis and in the case of post-operative hemorrhages. The following Examples illustrate the invention.

EXAMPLE 1

1 kg of comminuted cattle lung was stirred with 2 l of a 0.1 M pH 8.0 phosphate or borate buffer and the suspension was heated to 60° C. 13.2 Anson units (Anson, J. Gen. Physiol., 22 (1939) 79) of industrial protease obtained from Bacillus Alcalase (Novo Industri AS, Copenhagen, Denmark) or Bacillus Maxatase (Gist Brocades N.V., Delft, Netherlands) were added and the protein hydrolysis was carried out for 90 minutes at 60° C, while stirring intensively. The pH value was then adjusted to 1–2 with concentrated sulphuric acid and the residue was centrifuged off at high speed. The supernatant liquor was filtered through a fluted filter and the pH was then adjusted to 6 with sodium hydroxide solution. After filtration through a Seitz AS filter layer, a clear yellow organ extract solution was obtained. The average yield was $1.6 \times 10^6$ KIU/kg of lung, with an average inhibitory activity of 150–250 KIU/mg of protein.

138,000 KIU of the organ extract were fed, at a temperature of 4°–25° C, to a trypsin-"Sepharose" 4 B column, the accompanying proteins were eluted with a 0.1 M pH 4 acetate buffer (+ 0.3 M NaCl + 0.01 M $CaCl_2$) and the trypsin-inhibitor complex was dissociated with 0.1 M HCl (+ 0.5 M NaCl + 0.01 M $CaCl_2$) at pH 1.2. 128,000 KIU, corresponding to 92.7% of theory, were found in the eluate. After adjusting the pH value to 5–6 with potassium hydroxide solution, the inhibitor solution was concentrated in a rotary evaporator and desalinated over "Sephadex" G 25 using 0.1 M acetic acid or 0.1 M ammonium bicarbonate as the elution agent, and then lyophilized.

The desalination of the kallikrein-trypsin inhibitor can also be carried out, in good yield, with an ultrafiltration membrane.

Yield: 22.4 mg (121,500 KIU, corresponding to 88.1% of theory) Inhibitory activity: 5,450 KIU/mg of sample taken or 5,600 KIU/mg of protein.

EXAMPLE 2

1 kg of communited cattle lung was stirred with 2 l of a 0.1 M pH 7.0 phosphate buffer and the suspension was heated to 60° C. 19.5 Anson units of bacterial proteinase N (Röhm GmbH, Darmstadt, Federal Republic of Germany) were added and the protein hydrolysis was carried out for 90 minutes at 60° C, while stirring intensively. Further working up was carried out as in Example 1. The average yield was $1.6 \times 10^6$ KIU/kg of lung, with an inhibitory activity of 150 KIU/mg of protein.

150,000 KIU of the organ extract were pumped onto a trypsin-Sepharose 4 B column and the kallikrein-trypsin inhibitor was isolated as in Example 1. 137,000 KIU, corresponding to 91.3% of theory, were found in the eluate. After desalination over Sephadex G 25, 26.0 mg of inhibitor having an inhibitory activity of 4,600 KIU/mg were obtained (119,500 KIU, corresponding to 79.7% of theory).

EXAMPLE 3

1 kg of comminuted cattle lung was stirred with 2 l of a 0.1 M pH 7.0 phosphate buffer and the suspension was heated to 60° C. 15.4 Anson units of fungus proteinase P from Aspergillus (Rohm GmbH, Darmstadt, Federal Republic of Germany) were added and the protein hydrolysis was carried out for 90 minutes at 60° C, while stirring intensively. Further working up was carried out as in Example 1. The average yield was $1.7 \times 10^6$ KIU/kg of lung, with an inhibitory activity of 150–350 KIU/mg of protein.

151,000 KIU of the organ extract were pumped onto a trypsin-Sepharose 4 B column and the kallikrein-trypsin inhibitor was isolated as in Example 1. 160,000 KIU, corresponding to 106% of theory, were found in the eluate. After desalination over Sephadex G 25, 23.3 mg of inhibitor having an inhibitory activity of 5,074 KIU/mg were obtained (total 118,000 KIU, corresponding to 78.2% of theory).

EXAMPLE 4

1 kg of comminuted cattle lung was stirred with 2 l of a 0.1 M pH 7.0 phosphate buffer and the suspension was heated to 60° C. 14.3 Anson units of papain (Corolase S 50, Röhm GmbH, Darmstadt, Federal Republic of Germany) were added and the protein hydrolysis was carried out for 90 minutes at 60° C, while stirring intensively. Further working up was carried out as in Example 1. The average yield was $1.5 \times 10^6$ KIU/kg of lung, with an inhibitory activity of 150–250 KIU/mg of protein.

150,000 KIU of the organ extract were pumped onto a trypsin-Sepharose 4 B column and the kallikrein-trypsin inhibitor was isolated as in Example 1. 127,000 KIU, corresponding to 84.6% of theory, were found in the eluate. After desalination over Sephadex G 25, 24.1 mg of inhibitor having an inhibitory activity of 4,980 KIU/mg were obtained (total 120,000 KIU, corresponding to 80.0% of theory).

EXAMPLE 5

25 kg of comminuted cattle lung were stirred with 45 l of a 0.1 M pH 8.0 phosphate buffer and the suspension was heated to 60° C. 240 Anson units of Bacillus Alcalase were added and the protein hydrolysis was carried out for 90 minutes at 60° C, while stirring intensively. The pH value was adjusted to pH 1–2 with concentrated sulphuric acid and the precipitate was centrifuged off. The supernatant liquor was filtered and the pH was then adjusted to 6 with sodium hydroxide solution. After filtration through a Seitz AS filter layer, a clear yellow to brownish organ extract solution was obtained. The yield was $42.5 \times 10^6$ KIU, with an inhibitory activity of 240 KIU/mg of protein.

90,200 KIU of this organ extract were pumped onto a column which contained trypsin covalently bonded to a copolymer of acrylamide, N,N'-methylene-bis-acrylamide and maleic acid ("Enzygel" from Boehringer, Mannheim). The kallikrein-trypsin inhibitor was isolated as in Example 1. 83,3000 KIU, corresponding to 92.4% of theory, were found in the eluate. After desalination over Sephadex G 25, 14.5 mg of inhibitor having an inhibitory activity of 5,440 KIU/mg were obtained (total 78,900 KIU, corresponding to 87.3% of theory).

EXAMPLE 6

142,000 KIU of the organ extract from Example 5 were pumped onto a column which contained trypsin bonded to carboxymethylcellulose. The kallikrein-trypsin inhibitor was isolated as in Example 1. 132,000 KIU, corresponding to 93.0% of theory, were found in the eluate. After desalination over Sephadex G 25, 24.1 mg of inhibitor having an inhibitory activity of 5,310 KIU/mg were obtained (total 127,000 KIU, corresponding to 89.4% of theory).

EXAMPLE 7

75,500 KIU of the organ extract from Example 5 were pumped onto a column which contained trypsin bonded to cross-linked maleic anhydride. The kallikrein-trypsin inhibitor was isolated as in Example 1. 62,250 KIU, corresponding to 82.7% of theory, were found in the eluate. After desalination over Sephadex G 25, 27.1 mg of inhibitor having an inhibitory activity of 2,000 KIU/mg of sample weight, or 4,320 KIU/mg of protein, were obtained (total 54,200 KIU, corresponding to 59.3% of theory).

In the above Examples 1 to 4 Trypsin has been covalently bonded to Sepharose by the cyanogen bromide method according to the procedure of R. Axen, J. Porath and S. Ernback, Nature, 214 (1967) 1302.

As to Examples 5 to 7 we have to mention that Trypsin covalently bonded to copolymer of acrylamide, N,N'-methylene-bis-acrylamide and maleic acid has been purchased from Boehringer Mannheim company.

Trypsin bonded to crosslinked to maleic anhydride has been purchased from Merck Company, Darmstadt, Germany.

Trypsin bonded to Carboxymethylcelulose has been purchased from Merck Company, Darmstadt, Germany.

What is claimed is:

1. A process for the preparation of kallikrein-trypsin inhibitor, comprising subjecting an animal organ containing the inhibitor to proteolysis by a proteoytic enzyme at a temperature of at least about 40° C, adsorbing the resulting extract on carrier-bound trypsin and dissociating the resulting trypsin-inhibitor complex into trypsin and kallikrein-tryspin inhibitor.

2. The process according to claim 1, wherein said temperature is about 40° C to about 70° C.

3. The process according to claim 1, wherein the temperature is about 60° C.

4. The process according to claim 1, wherein the proteolysis is effected at a pH of from about pH 5 to about pH 10.

5. The process according to claim 1, wherein the protedytic enzyme is selected from the group consisting of proteolytic enzyme isolated from microorganisms, fungi and plants.

6. The process according to claim 5, wherein said proteolytic enzyme is selected from the group consisting of subtilisin, Bacillus Alcalase, Bacillus Maxatase, papain, fungus proteinase P from Aspergillus and bacterial proteinase No.

7. The process according to claim 1, wherein the carrier-bound trypsin is trypsin which is covalently bound to a carrier selected from the group consisting of Sepharose, a copolymer of acrylamide N,N'-methylene-bis-acrylamide and maleic acid, carboxymethycellulose, and cross-linked maleic anhydride.

8. The process according to claim 1, wherein the animal organ is an organ of a ruminant.

9. The process according to claim 8, wherein the animal organ is lung, parotid, liver or pancreas.

10. The process according to claim 9, wherein the animal organ is cattle lung.

11. The process according to claim 1, wherein said extract is passed through a column containing said carrier-bound trypsin, hydrolyzed protein is eluted from the column with an acetate buffer of about pH 4 as an eluant, and then the trypsin-inhibitor complex is dissociated.

12. The process according to claim 1, wherein said trypsin-inhibitor complex is dissociated by treatment with a dilute mineral acid.

* * * * *